United States Patent [19]
Itagaki et al.

[11] Patent Number: 6,011,169
[45] Date of Patent: Jan. 4, 2000

[54] PROCESS FOR PRODUCING OPTICALLY ACTIVE CYCLOPROPANECABOXYLIC ACID ESTERS

[75] Inventors: Makoto Itagaki, Takatsuki; Gohfu Suzukamo, Suita, both of Japan

[73] Assignee: Sumitomo Chemical Company, Limited, Osaka, Japan

[21] Appl. No.: 09/113,502

[22] Filed: Jul. 10, 1998

[30] Foreign Application Priority Data

Jul. 14, 1997 [JP] Japan ................................ 9-188185

[51] Int. Cl.$^7$ .................................................. C07C 69/74
[52] U.S. Cl. ............................................................. 560/124
[58] Field of Search ............................................. 560/124

[56] References Cited

PUBLICATIONS chem abstracts 1991:101151, Lowenthal et al, 1990.
Aratani, Pure & Appl. Chem., vol. 57, No. 12, pp. 1839–1844.
Fritschi, Helvetica Chimica Acta, vol. 71, pp. 1553–1565, (1988).
Evans, J. Am. Chem. Soc. vol. 113, pp. 726–728, (1991).
Lowenthal, Tetrahedron Letters, vol. 32, No. 50, pp. 7373–7376, (1991).
Kanemasa, Tetrahedron Letters, vol. 35, No. 43, pp. 7985–7988, (1994).
Gant, Tetrahedron Letters, vol. 36, No. 48, pp. 8745–5748, (1995).
Lowenthal, Tetrahedron Letters, vol. 31, No. 42, pp. 6005–6008 (1990).
Corey, Tetrahedron Letters, vol. 33, No. 45, pp. 6807–6810 (1992).
Database WPI, Section Ch, Week 9742, AN 97–453974, XP–002083088, Aug. 12, 1997 (abstract).
Database WPI, Section Ch, Week 9702, AN 97–017330, XP–002083089, Oct. 29, 1996 (abstract).
Muller et al., Helvetica Chimica Acta, vol. 74, pp. 232–240, XP–002083087 (1991).
Lowenthal, et al., Tetrahedron Letters, vol. 31, No. 42, pp. 6005–6008, XP–002021203 (1990).

*Primary Examiner*—Samuel Barts
*Attorney, Agent, or Firm*—Birch, Stewart, Kolasch & Birch, LLP

[57] ABSTRACT

A process for producing an optically active cyclopropanecarboxylic acid ester which is characterized by reacting a prochiral olefin with a diazoacetic acid ester in the presence of a copper complex obtained by reacting an optically active bisoxazoline ligand with a copper compound.

10 Claims, No Drawings

PROCESS FOR PRODUCING OPTICALLY ACTIVE CYCLOPROPANECABOXYLIC ACID ESTERS

BACKGROUND OF THE INVENTION

1. Field of the Invention

The present invention Relates to a process for producing optically active cyclopropanecarboxylic acid esters.

2. Description of Related Arts

The optically active cyclopropanecarboxylic acid esters are important compounds as intermediates for pharmaceuticals and pesticides. For example, (+)-2,2-dimethyl-3-(2-methyl-1-propenyl)cyclopropanecarboxylic acid, also known as chrysanthemum-monocarboxylic acid, constitutes the acid component of synthetic pyrethroid insecticides.

Conventionally, asthemethods for directly producing optically active cyclopropanecarboxylic acid esters by synthetic technique, for example, a method has been known in which a prochiral olefin is reacted with a diazoacetic acid ester in the presence of an asymmetric copper complex using an optically active bis [2-(4,5-diphenyl-1,3-oxazolinyl)] methane as the ligand (Tetrahedron Lett., 32, 7373 (1991)).

Since, however, this method has problems in that the raw material used for synthesizing the ligand is expensive and the method for synthesizing the ligand is complicated, this method can not always be said to be an industrially advantageous.

The present inventors have completed the present invention as a result of an extensive study conducted for the purpose of developing a process for producing optically active cyclopropanecarboxylic acid esters in the presence of a copper complex which is obtainable by reacting a copper compound with a bisoxazoline compound as the ligand which is produced by a simple process from an inexpensive optically active amino acid.

SUMMARY OF THE INVENTION

The present invention provides a process for producing an optically active cyclopropanecarboxylic acid ester of the formula [I]:

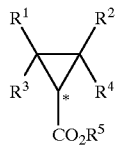

[I]

wherein $R^1$, $R^2$, $R^3$ and $R^4$ are the same or different and represent hydrogen atom, an alkyl group which may be substituted with a halogen atom, an alkenyl group which may he substituted with a halogen atom or an alkoxycarbonyl group., with the proviso that when $R^1$ and $R^2$ represent the same group, then $R^3$ and $R^4$ represent different groups, $R^5$ represents an alkyl group having 1 to 6 carbon atoms, cycloalkyl group which may be substituted with a lower alkyl group, a benzyl group or a phenyl group which may be substituted with an alkyl group or an alkoxy group, and asterisk * designates an asymmetric carbon atom, which comprises reacting a prochiral olefin of the formula [II]:

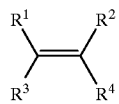

[II]

wherein $R^1$, $R^2$, $R^3$ and $R^4$ are as the same as defined above, with a diazoacetic acid ester of the formula [III]:

$$N_2CHCO_2R^5 \quad [III]$$

wherein $R^5$ is the same as defined above, in the presence of a copper complex obtained by reacting an optically active bisoxazoline ligand of the formula [IV]:

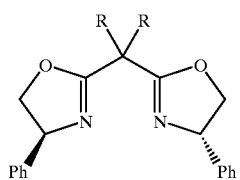

[IV]

wherein R represents hydrogen atom or alkyl group having 1 to 3 carbon atoms and Ph represents a phenyl group, with a copper compound.

DETAILED DESCRIPTION

The present invention is characterized in that, in the reaction of the prochiral olefin [II] with the diazoacetic acid ester [III], a copper complex is used which is obtained by reacting an optically active bisoxazoline ligand [IV] with a copper compound.

The copper compound to be used in the present invention includes, for example, monovalent or divalent copper compounds such as copper trifluoromethanesulfonate, copper acetate, copper bromide, copper chloride and the like, copper (II) trifluoromethanesulfonate being preferred. These copper compound can be used independently or in combination of two or more.

Formula [IV] represents a relative configuration of the optically active bisoxazoline ligands of the present invention. An optically active bisoxazoline ligand of the formula [IV] having 4(R)-phenyl-2-oxazoline moieties or 4(S)-phenyl-2-oxazoline moieties can be used in the present invention.

Specific examples of the optically active bisoxazoline ligand [IV] include:
bis[2-[4(R)-phenyl-2-oxazoline]]methane,
2,2-bis[2-[4(R)-phenyl-2-oxazoline]]propane,
3,3-bis[2-[4(R)-phenyl-2-oxazoline]]heptane and the like and compounds having (S) configuration in place of (R) in the above-described compounds.

These bisoxazoline ligands [IV] can be obtained by known methods including, for example, a method in which (R)-phenylglycinol is reacted with dimethyl malonate to form a diamido compound, which is chlorinated by thionyl chloride, and reacted with an ethanol-tetrahydrofuran solution of sodium hydroxide to give bis[2-[4(R)-phenyl-2-oxazoline]]methane (Helvetica Chimica Acta, vol. 74, (1991)).

The copper complex used in the present invention can be obtained by reacting the copper compound described as above with the bisoxazoline ligand [IV].

In this reaction, a solvent is usually used and such solvent includes, for example, halogenated hydrocarbons such as methylene chloride, 1,2-dichloroethane, chloroform, carbon tetrachloride and the like, aromatic hydrocarbons such as benzene, toluene, xylene, ester compounds such as ethyl acetate and the like, and so on. Alternatively, the prochiral olefin [II] to be used in the next step can be used as a solvent in this step.

The amount to be used of the solvent is usually 5–500 parts by weight per 1 part by weight of the copper compound.

The amount to be used of the bisoxazoline ligand [IV] is usually 0.8–5 moles, preferably 1–2 moles per mole of the copper compound.

The reaction of the copper compound with the bisoxazoline ligand [IV] is usually carried out in an inert gas atmosphere such as argon, nitrogen or the like. From the viewpoint of the reaction yield, the above reaction is preferably carried out in the absence of water.

The reaction temperature is not particularly limited and may usually be in a range of 0–50° C.

The copper complex thus obtained may be isolated or may be used as it is in the reaction of the prochiral olefin [II] with diazoacetic acid ester [III] without isolation.

The amount to be used of the copper complex is usually 0.0001–0.01 mole, preferably 0.0002–0.002 mol in terms of copper atom per mol of diazoacetic acid ester [III].

In the present invention, when divalent copper(II) compound is used for preparing the complex, it is not necessary to reduce the copper compound to a corresponding monovalent copper(I) compound using a reducing agent such as phenylhydrazine or the like.

The diazoacetic acid esters [III] used in the present invention can be obtained by known methods by subjecting, for example, the corresponding amino acid ester to the diazotization reaction and extracting the product with halogenated hydrocarbon such as chloroform or the like. The product can be isolated by distillation or the like, if necessary.

In the diazoacetic acid esters of the formula [III], $R^5$ represents an alkyl group having 1 to 6 carbon atoms,
  a (C3–C6)cycloalkyl group which may be substituted with a (C1–C3)lower alkyl group,
  a benzyl group or
  a phenyl group which may be substituted with a (C1–C3) alkyl group or a (C1–C3)alkoxy group.

Specific examples of $R^5$ include methyl, ethyl, propyl, isopropyl, butyl, isobutyl, s-butyl, t-butyl, n-pentyl, n-hexyl, l-menthyl, d-menthyl, benzyl, cyclohexyl, phenyl, m-methylphenyl, m-methoxyphenyl, 3,5-dimethylphenyl, 3,5-dimethoxyphenyl, 4-methyl-2,6-di-t-butylphenyl and the like.

In the prochiral olefin of the formula [II], $R^1$, $R^2$, $R^3$ and $R^4$ are the same or different and represent a hydrogen atom, a (C1–C5)alkyl group which may be substituted with a halogen atom, a (C2–C5)alkenyl group which may be substituted with a halogen atom or a (C2–C5) alkoxycarbonyl group.

Specific examples the prochiral olefin of the formula [II] include propene, 1-butene, isobutylene, 2,5-dimethyl-2,4-hexadiene, 2-chloro-5-methyl-2,4-hexadiene, 2-fluoro-5-methyl-2,4-bexadiene, 1,1,1-trifluoro-5-methyl-2,4-hexadiene, 2-mothoxycarbonyl-5-methyl-2,4-hexadiene, 1,1-difluoro-4-methyl 1,3-pentadiene, 1,1-dichloro-4-methyl-1,3-pentadiene, 1,1-dibromo-4-methyl-1,3-pentadiene, 1-chloro-1-fluoro-4-methyl-1,3-pentadiene, 1-fluoro-1-bromo-4-methyl-1,3-pentadiene, 1,1,1-trichloro-4-methyl-3-pentene, 1,1,1-tribromo-4-methyl-3-pentene, 2,3-dimethyl-2-pentene, 2-bromo-2,5-dimethyl-4-hexene, 2-chloro-2,5-dimethyl-4-hexene and the like, 2,5-dimethyl-2,4-hexadiene being preferred.

The amount to be used of the prochiral olefin [II] is usually 2 moles or more, preferably 5–50 moles per mol of the diazoacetic acid ester [III].

According to the present invention, the prochiral olefin [II] is reacted with the diazoacetic acid ester [III] in the presence of the copper complex. Specific methods include, for example, a method wherein the diazoacetic acid ester [III] dissolved in a solvent is added to a mixture of the copper complex as obtained in a similar manner as described above and the prochiral olefin [III].

The solvent includes, for example, halogenated hydrocarbons such as dichloromethane, 1,2-dichloroethane, chloroform, carbon tetrachloride and the like, aliphatic hydrocarbons such as hexane, heptane, cyclohexane and the like, aromatic hydrocarbons such as benzene, toluene, xylene and the like, esters such as methyl acetate, ethyl acetate and the like. Alternatively, the prochiral olefin [II] can be used as the solvent. These can be used in combination.

The amount to be used of the solvent is usually 2–30 parts, preferably 5–20 parts by weight per 1 part by weight of the diazoacetic acid ester [III].

The reaction of the prochiral olefin [II] with the diazoacetic acid ester [III] is usually carried out in an inert gas atmosphere such as argon, nitrogen or the like. From the viewpoint of the reaction yield, the above reaction is preferably carried out in the absence of water.

The reaction temperature is not particularly limited and may be the boiling point of the solvent, when used, or usually in a range of 0–100° C., preferably of 5–80° C.

The optically active cyclopropanecarboxylic acid esters [I] obtained in the above reaction can be isolated, by conventional methods such as distillation, column chromatography and the like, if necessary.

The stereochemical configuration with respect to the asterisked carbon atom at 1-position of the cyclopropane ring in the optically active cyclopropanecarboxylic acid esters [I] can be controlled by using the copper complex of the present invention.

Specific compounds of the optically active cyclopropanecarboxylic acid esters [I] obtained in the present intention includes, for example, optically active isomers of 2-methylcyclopropanecarboxylic acid ester,
2,2-dimethylcyclopropanecarboxylic acid ester,
2,2-dimethyl-3-(2-methyl-1-propenyl)-cyclopropanecarboxylic acid ester,
2,2-dimethyl-3-(2,2-dichloro-1-ethenyl) cyclopropanecarboxylic acid ester,
2,2-dimethyl-3-(2,2,2-trichloroethyl) cyclopropanecarboxylic acid ester,
2,2-dimethyl-3-(2,2,2-tribromoethyl)clopropanecarboxylic acid ester,
2,2-dimethyl-3-(2,2-dibromo-1-ethenyl) cyclopropanecarboxylic acid ester,
2,2-dimethyl-3-(2,2-difluoro-1-ethenyl) cyclopropanecarboxylic acid ester,
2,2-dimethyl-3-(2-fluoro-2-chloro-1-ethenyl) cyclopropanecarboxylic acid ester,
2,2-dimethyl-3-(2-fluoro-2-bromo-1-ethenyl)-cyclopropanecarboxylic acid ester,
2,2-dimethyl-3-(2-fluoro-1-propenyl) cyclopropanecarboxylic acid ester,
2,2-dimethyl-3-(2-chloro-1-propenyl) cyclopropanecarboxylic acid ester, 2,2-dimethyl-3-(2-chloro-2,2,2-trifluoromethylethenyl) cyclopropanecarboxylic acid ester, 2,2-dimethyl-3-(2-methoxyearbonyl-1-propenyl)-cyclopropanecarboxylic acid ester, 2,2-dimethyl-3-(2-chloro-2-methyl) propylcyclopropanecarboxylic acid ester, 2,2-dimethyl-3-(2-bromo-2-methyl) propylcyclopropanecarboxylic acid ester and the like.

The alcohol residue for $R^5$ in the optically active cyclopropanecarboxylic acid esters [I] includes, for example, methyl, ethyl, n-propyl, i-propyl, i-butyl, t-butyl, cyclohexyl, menthyl, 4-methyl-2,6-di-t-butylphenyl and the like.

The optically active cyclopropanecarboxylic acid esters [I] thus obtained can be converted into optically active cyclopropanecarboxylic acids having a hydrogen atom as the substituent $R^5$ by subjecting the ester to ester-hydrolysis or ester-thermolysis reaction according to a conventional method.

The optically active cyclopropanecarboxylic acid esters [I] produced according to the present process can be used in the ester-hydrolysis or ester-thermolysis reaction without isolation.

The methods for the above described ester-hydrolysis are not particularly limited and may be effected according to the known process including, for example, the hydrolysis using an alkali metal hydroxide such as sodium hydroxide, potassium hydroxide or the like, the thermal decomposition by heating in the presence of an acid catalyst and so on.

According to the present invention, the optically active cyclopropanecarboxylic acid esters [I] can be produced with good selectivity by carrying out the reaction of the prochiral olefin [II] with the diazoacetic acid ester [III] in the presence of the copper complex prepared from the optically active bisoxazoline and the copper compound.

EXAMPLES

The present invention will now be illustrated in more detail by reference of Examples, which should not be construed as a limitation upon the scope of the present invention.

Example 1

In a 50 ml Schlenk's tube purged with nitrogen were placed 18.05 mg (0.05 mmol) of copper(II) trifluoromethanesulfonate, 16.9 mg (0.055 imol) of bis[2-[4(R)-phenyl-2-oxazolinel]]methane and 14 ml of 1,2-dichloroethane, and the resulting mixture was stirred at room temperature for 10 minutes. After adding 6.0 g (55 mmol) of 2,5-dimethyl-2,4-hexadiene, 1.1 g (10 mmol) of ethyl diazoacetate was added dropwise at 25° C. over 2 hours. The stirring wascontinued at 25° C. for 1 hour after completion of the addition of ethyl diazoacetate. The amount of produced ethyl chrysanthemum-monocarboxylate was found 1.58 g as determined by gas chromatography. The yield based on ethyl diazoacetate was 80.5% and the trans/cis was 72/28. After evaporating 2,5-dimethyl-2,4-hexadiene (boiling point:51° C./30 mmHg), a 1 g aliquot of the concentrated solution was sampled and subjected to alkaline hydrolysis by adding 10 ml of aqueous 1N sodium hydroxide solution and 5 ml of ethanol, and, stirring at 100° C. for 1 hour. The obtained chrysanthemum-monocarboxylic acid was esterified with 1(−)-menthol and the produced diastereomeric esters were analyzed by gas chromatography.

The optical purity of the trans-isomer [ethyl (1R, 3R)-trans-2,2-dimethyl-3-(2-methyl-1-propenyl) cyclopropanecarboxylate was 64% e.e. and the optical purity of the cis-isomer [ethyl (1R,3S)cis-2,2-dimethyl-3-(2-methyl-1-propenyl)cyclopropanecarboxylate was 39% e.e.

Example 2

The procedure in Example 1 was repeated except that the reaction solvent was changed from 1,2-dichloroethane to ethyl acetate. The yield of ethyl chrysanthemum-monocarboxylate baedonethyl diazoacetate was 78.7%, the trans/cis ratio was 72/28, the optical purity of the trans-isomer was 65% e.e. and the optical purity of the cis-form was 35% e.e.

Example 3

The procedure in Example 1 was repeated except that ethyl diazoacetate was replaced by t-butyl diazoacetate. The obtained amount of t-butyl chryeanthemum-monocarboxylate was 1.8 g, the yield was 81.4% and the trans/cis ratio was 82/18. After evaporating 2,5-dimethyl-2, 4-hexadiene, a 1 g aliquot of the concentrated solution was sampled and subjected to optical purity determination by liquid chromatography. The optical purity of the trans-isomer was 77% e.e. and the optical purity of the cis-isomer was 57% e.e.

Example 4

The procedure in Example 1 was repeated except that ethyl diazoacetate was replaced by irobutyl diazoacetate. The obtained amount of isobutyl chrysanthemum-monocarboxylate was 1.2 g, the yield was 54.4% and the trans/cis ratio was 76/24. The calculation of optical purity was performed according to Example 1. The optical purity of the trans-isomer was 67% e.e. and the optical purity of the cis-isomer was 31% e.e.

Example 5

The procedure in Example 1 was repeated except that bis[2-[4(R)-phenyl-2-oxazoline]]methane was replaced by 18.4 mg (0.055 mmol) of 2,2-bis[2-[4(R)-phenyl-2-oxazolinel]]propane. The obtained amount of ethyl chrysanthemum-monocarboxylate was 1.55 g, the yield was 78.8% and the trans/cis ratio was 69/31. The optical purity of the trans-isomer was 67% e.e. and the optical purity of the cis-isomer was 21.8% e.e.

Comparative Example 1

The procedure in Example 1 was repeated except that bis[2-[4(R)-phenyl-2-oxazoline]]methane was replaced by 13.1 mg (0.055 mmol) of bis[2-[4(R)-isopropyl-2-oxazolinel]]methane. The obtained amount of ethyl chrysanthemum-monocarboxylate was 1.28 g, the yield was 65.3% and the trans/cis ratio was 63/37. The optical purity of the trans-isomer was 36.4% e.e. and the optical purity of the cis-isomer was 24.2% e.e.

Comparative Example 2

The procedure in Example 1 was repeated except that bis[2-[4(R)-phenyl-2-oxazoline]]methane was replaced by 16.0 mg (0.055 mmol) of bis[2-[4(R)-t-butyl-2-oxazolinel ]]methane. The obtained amount of ethyl chrysanthemum-monocarhoxylate was 1.29 g, the yield was 66.0% and the trans/cis ratio was 66/34. The optical purity of the trans-isomer was 14.9% e.e. and the optical purity of the cis-isomer was 0.9% e.e.

Comparative Example 3

The procedure in Example 1 was repeated except that bis[2-[4(R)-phenyl-2-oxazoline]]methane was replaced by 18.39 mg (0.055 mmol) of bis[2-[4(R)-methyl,5(S)-phenyl-2-oxazoline]]methane. The obtained amount of ethyl chrysanthemum-monocarboxylate was 1.32 g, the yield was 67.1% and the trans/cis ratio was 65/35. The optical purity of the trans-isomer was 32.2% e.e. and the optical purity of the cis-isomer was 18.4% e.e.

What is claimed is:

1. A process for producing an optically active cyclopropanecarboxylic acid ester of the formula [I]:

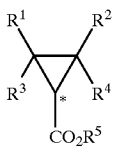

[I]

wherein $R^1$, $R^2$, $R^3$ and $R^4$ are the same or different and represent a hydrogen atom, an alkyl group which may be substituted with a halogen atom, an alkenyl group which may be substituted with a halogen atom or an alkoxycarbonyl group, with the proviso that when $R^1$ and $R^2$ represent the same group, then $R^3$ and $R^4$ represent different groups, $R^5$ represents an alkyl group having 1 to 6 carbon atoms, a cycloalkyl group which may be substituted with a lower alkyl group, a benzyl group or a phenyl group which may be substituted with an alkyl group or an alkoxy group, and an asterisk * designates an asymmetric carbon atom, which comprises reacting a prochiral olefin of the formula [II]:

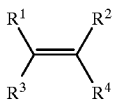

[II]

wherein $R^1$, $R^2$, $R^3$ and $R^4$ are as defined above, with a diazoacetic acid ester of the formula [III]:

$N_2CHCO_2R^5$ [III]

wherein $R^5$ is as defined above, in the presence of a copper complex obtained by reacting an optically active bisoxazoline ligand of the formula [IV]:

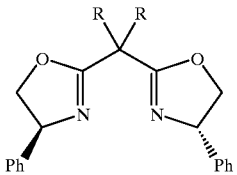

[IV]

wherein R represents a hydrogen atom or an alkyl group having 1 to 3 carbon atoms and Ph represents a phenyl group, with a copper compound.

2. The process according to claim 1, wherein the copper compound is copper (II) compound.

3. The process according to claim 1, wherein the copper compound is copper (II) trifluoromethanesulfonate.

4. The process according to claim 1, 2 or 3, wherein the prochiral olefin is 2,5-dimethyl-2,4-hexadiene.

5. The process of claim 1, wherein the optically active bisoxazoline ligand (IV) is selected from the group consisting of bis[2-[4(R)-phenyl-2-oxazoline]]methane, 2,2-bis[2[4(R)-phenyl-2-oxazoline]]propane, 3,3-bis[2-[4(R)-phenyl-2-oxazoline]]heptane, bis[2-[4(S)-phenyl-2-oxazoline]]methane, 2,2-bis[2-[4(S)-phenyl-2-oxazoline]]propane, and 3-3-bis[2-[4(S)-phenyl-2-oxazoline]] heptane.

6. The process of claim 1, wherein the bisoxazoline ligand (IV) is present in an amount of 1–2 moles per mole of the copper compound.

7. The process of claim 1, wherein the copper complex is present in an amount of 0.0002–0.002 moles in terms of copper atom per mole of the diazoacetic acid ester.

8. The process of claim 1, wherein the prochiral olefin of the formula (II) include propene, 1-butene, isobutylene, 2,5-dimethyl-2,4-hexadiene, 2-chloro-5-methyl-2,4-hexadiene, 2-fluoro-5-methyl-2,4-hexadiene, 1,1,1-trifluoro-5-methyl-2,4-hexadiene, 2-methoxycarbonyl-5-methyl-2,4-hexadiene, 1,1-difluoro-4-methyl-1,3-pentadiene, 1,1-dichloro-4-methyl-1,3-pentadiene, 1,1-dibromo-4-methyl-1,3-pentadiene, 1-chloro-1-fluoro-4-methyl-1,3-pentadiene, 1-fluoro-1-bromo-4-methyl-1,3-pentadiene, 1,1,1-trichloro-4-methyl-3-pentene, 1,1,1-tribromo-4-methyl-3-pentene, 2,3-dimethyl-2-pentene, 2-bromo-2,5-dimethyl-4-hexene, and 2-chloro-2,5-dimethyl-4-hexene.

9. The process of claim 1, wherein the prochiral olefin is present in an amount from 5 to 50 moles per mole of the diazoacetic acid ester.

10. The process of claim 1, wherein the optically active cyclopropanecarboxylic acid ester (I) is selected from the group consisting of optically active isomers of 2-methylcyclopropanecarboxylic acid ester, 2,2-dimethylcyclopropanecarboxylic acid ester, 2,2-dimethyl-3-(2-methyl-1-propenyl)cyclopropanecarboxylic acid ester, 2,2-dimethyl-3-(2,2-dichloro-1-ethenyl) cyclopropanecarboxylic acid ester, 2,2-dimethyl-3-(2,2,2-trichloroethyl)cyclopropanecarboxylic acid ester, 2,2-dimethyl-3-(2,2,2-tribromoethyl)clopropanecarboxylic acid ester, 2,2-dimethyl-3-(2,2-dibromo-1-ethenyl) cyclopropanecarboxylic acid ester, 2,2-dimethyl-3-(2,2-difluoro-1-ethenyl)cyclopropanecarboxylic acid ester, 2,2-dimethyl-3-(2-fluoro-2-chloro-1-ethenyl) cyclopropanecarboxylic acid ester, 2,2-dimethyl-3-(2-fluoro-2-bromo-1-ethenyl)cyclopropanecarboxylic acid ester, 2,2-dimethyl-3-(2-fluoro-1-propenyl) cyclopropanecarboxylic acid ester, 2,2-dimethyl-3-(2-chloro-1-propenyl)cyclopropanecarboxylic acid ester, 2,2-dimethyl-3-(2-chloro-2,2,2-trifluoromethylethenyl) cyclopropanecarboxylic acid ester, 2,2-dimethyl-3-(2-methoxycarbonyl-1-propenyl)cyclopropanecarboxylic acid ester, 2,2-dimethyl-3-(2-chloro-2-methyl) propylcyclopropanecarboxylic acid ester, and 2,2-dimethyl-3-(2-bromo-2-methyl)propylcyclopropanecarboxylic acid ester.

* * * * *